United States Patent [19]

Holzmann

[11] 4,247,540

[45] Jan. 27, 1981

[54] THERAPEUTIC AGENT

[76] Inventor: Gunter Holzmann, Casilla 391, Santa Cruz, Bolivia

[21] Appl. No.: 7,936

[22] Filed: Jan. 31, 1979

Related U.S. Application Data

[63] Continuation-in-part of Ser. No. 855,714, Nov. 29, 1977, abandoned, which is a continuation-in-part of Ser. No. 653,356, Jan. 29, 1976, abandoned, which is a continuation-in-part of Ser. No. 434,107, Jan. 17, 1974, abandoned, which is a continuation-in-part of Ser. No. 298,573, Oct. 18, 1972, abandoned.

[51] Int. Cl.$^3$ .................... A61K 35/12; A61K 35/56
[52] U.S. Cl. ...................................................... 424/95
[58] Field of Search ........................................ 424/95

Primary Examiner—Jerome D. Goldberg
Attorney, Agent, or Firm—McAulay, Fields, Fisher, Goldstein & Nissen

[57] ABSTRACT

A Therapeutic Agent, comprising an aqueous extract material from the venom sac of ants from the genus Pseudomyrmex species *triplarinus,* is injected into a patient with the result that there is a remission of pain and other symptoms due to such auto-immune ailments as rheumatoid arthritis without the discomfort experienced from venom injected into a patient. The active agent is determined to be a composition of a polysaccharide nature.

4 Claims, 7 Drawing Figures

FIG. I.

PURIFICATION OF POLYSACCHARIDE FROM NATIVE ANT VENOM

THERAPEUTIC AGENT

REFERENCE TO RELATED APPLICATION

This application is a continuation-in-part of copending application Ser. No. 855,714, filed Nov. 29, 1977 which is a continuation-in-part of Ser. No. 653,356, filed Jan 29, 1976 which is a continuation-in-part of application Ser. No. 434,107, filed Jan. 17, 1974 which in turn is a continuation-in-part of application Ser. No. 298,573, filed Oct. 18, 1972, all of said patent applications being entitled "Therapeutic Agent" and all of said applications now abandoned.

BACKGROUND OF THE INVENTION

This invention relates in general to a composition and method for relieving the symptoms of such auto-immune ailments as rheumatoid arthritis or asthma and, more particularly, to a composition that can be injected into a person who suffers from such with the result that, without apparent significant side effects, there is material and significant remission of symptoms. The nature of rheumatoid arthritis and asthma are such that one familiar with them would be led to conclude that other auto-immune ailments which also involve symptomatic inflammation of tissues will also respond to treatment according to the present invention: multiple sclerosis (nerve tissue), lupus erythematosus (kidneys), scleroder- mata (skin), arteritis, and other somewhat rare ailments classified as connective tissue diseases, or immune complex diseases.

Using ant stings as a means of treatment is impossible, not only because live ants cannot be shipped or handled efficiently, but because of the unbearable pain of the many stings necessary.

The extract used formerly solved these problems, but still produced certain discomfort, and, although harmless, in some sensitive patients there was a slight local irritation at the point of injection.

The new, purified extract reduces those local irritations of the skin to practically zero. There are a number of theories for the etiology of rheumatoid arthritis including the probability that it is an auto-immunological ailment which requires the existance of an antibody or RA factor in the blood. (Note RA and RF are used interchangeably in this disclosure). The presence of the RA factor antibody is well known and widely used as a confirming test for arthritis. A rheumatoid arthritis causative agent has not been isolated.

As noted above, because the present invention works on a second auto-immune ailment, and in view of certain results of laboratory tests in vitro with components of the human body complement system and tests on at least one patient, it is believed that similar auto-immune ailments will also respond to treatment.

It is too notorious to require further explication here that the pain and discomfort due to arthritis and asthma is a major disabling factor for large numbers of people. Even without actually curing these diseases, a remission of the symptoms would permit many individuals to lead more profitable and more fulfilling lives. Other auto-immune ailments if untreated, can cause death.

It is an object of this invention to provide a means for relieving pain, swelling and other pathological symptoms due to rheumatoid arthritis.

It is a still further object of this invention to provide such a means that is easy to employ and is relatively safe.

It is a still further object to provide such a means which has practical utility in that side effects such as pain are relatively mild or non-existant. It is a related object to provide such means which does not operate as a stress agent, that is which does not stimulate the adrenal gland to produce cortical steroids: an anti-stress as well as anti-inflammatory agent whose depletion, caused by continued stimulation of the adrenal gland, can result in the development of life threatening adrenal crisis on the occurrence of otherwise harmless everyday stresses, as occurs with other drugs on the market.

BRIEF DESCRIPTION

In brief, this invention is in the use of an active agent found in an extract of materials from the venom sac of certain ants, particularly ants of the genus *Pseudomyrmex* species *triplarinus* to provide remission of symptoms in rheumatoid arthritis.

The extract is obtained by crushing the abdomen of the ant. The crushed abdomen are then mixed with an aqueous solvent and the resulting solution filtered, purified, and adjusted to provide a concentration effective for injection into a patient. The extract containing the therapeutic agent is injected subcutaneously into the patient wherein, apparently without significant side effects, it causes remission of arthritic symptoms and appears to significantly decrease the RA factor (measure of an antibody normally associated with rheumatoid arthritis). Similar treatment will also cause remission of symptoms for asthma.

An aqueous saline solution (physiological solution) is normally employed as the carrier as this has been found to be compatable with the extract as well as the human body.

In order to identify the active agent in the extract, the human complement system is used as a test of activity of purified substances. The validity of this method of assaying was confirmed by a number of actual tests on humans and rats.

DESCRIPTION OF THE PREFERRED EMBODIMENTS

The ant *Pseudomyrmex triplarinus* is found in certain parts of tropical South America. This species of ant is generally limited in its distribution to South America and belongs to a highly specialized group of ants all of which are restricted in their nesting habits to trees of the genus Triplaris which plant group is limited to the American tropics.

These ants belong to a sub-family Pseudomyrmiciniae. More specifically the ant employed in the tests is the worker (sterile female), genus Pseudomyrmex, species *triplarinus;* sub-family Pseudomyrmiciniae, and family Formicidae.

This sub-family has an unusual evolutionary history. It is difficult to determine the relationships of this sub-family and, indeed, there is no agreement on where it should be placed in the evolution of ants. It clearly belongs to the family Formicidae; which is the ant family. But beyond that it is not clear what its ancestral strain was or how its ancestral strain may have been related to the ancestral strains of other ants.

It is probably fair to say that, within the context of agreeing that these are indeed ants, they appear to be totally unrelated to the rest of the ants. They are unrelated in the sense that some of their habits and in particular their anatomy diverge pronouncedly from the habits and the anatomy of other ants. This is one of the reasons for the conclusion that the venom of the ants of the *triplarinus* species of ant, is unrelated to the venom of other insects including the venom of any other group of ants except perhaps for some of the species in their own sub-family Pseudomyrmicinae.

Accordingly, it is reasonable to believe that other species of this sub-family may be found to have venom with similar therapeutic properties.

The sting of these ant causes severe discomfort to anyone receiving it. However, there is apparently a constituent of the venom which, when injected repeatedly into someone who suffers from rheumatoid arthritis, leads to remission of pain and swelling and also to increased motility of the joints without causing the severe discomfort normally associated with stings. Similar treatment will also provide remission of symptoms of asthma. It appears that not only is the particular constituent an effective therapeutic agent, but an aqueous extract of the venom sac as well, in appropriate concentrations and doses, can be used to achieve the objects of this invention.

EXTRACTION OF THE ACTIVE AGENT

Method I (Aqueous Extraction)

In one method that has been used to make an appropriate composition for injecting into a patient, the abdomens are separated from the ants. The abdomen contains the venom sac. A fixed number of separated abdomens are then macerated (stirred, squeezed and crushed) in saline physiological solution to dissolve the soluble parts in the physiological solution. The mixture is then filtered, removing all insoluble constituents. The result is a solution of portions of the venom and other abdominal juices which are soluble in physiological solution.

More specifically, a presently preferred mode of preparing an effective agent involves the following steps: (1) the dissected abdomens are macerated in a saline physiological solution, (2) the result is filtered through a No. 1 gauge filter and the filter is worked three times with physiological solution, (3) the result is diluted with saline physiological solution to a concentration equivalent to the venom from ten ants in one cubic centimeter of solution, (4) controls are taken for bacteriological and microscopic analysis, and (5) after sterility is proven the solution is stored at one to two degrees Centigrade. The solution can be held in sterile ampoules for use.

USE OF ACTIVE AGENT FOR SYMPTOMATIC RELIEF OF RHEUMATOID ARTHRITIS

Discussion of Initial Test Results for Utility

In a number of early tests, the crushed and filtered abdomen of one hundred ants extracted according to Method I and diluted with physiological solution to provide twenty cubic centimeters (20 c.c.) of mixture, was used. The resulting concentration is the content of five venom sacs in one c.c. In an initial series of tests, the injections generally started with an amount of solution containing the venom provided by 0.5 ants. Such an amount is called herein 0.5 UF. Doses were given daily to step the amount up over a period of about ten days to a level where doses are equal to the venom from approximately five to ten ants. At first 0.1 c.c. was injected in the upper arm in order to determine the patient's sensitivity to the venom and to prevent anaphylactic reaction. If no adverse reaction was observed, injections then were administered at regular intervals and increasing doses, starting with 0.5 UF. All injections were administered subcutaneously or intradermically. With good tolerance, doses were given daily for about 10 days, increasing the concentration for the last 5 days to 10 UF daily, according to each individual case. The reaction of the skin to these injections is similar to the reaction of the skin toward a sting from the ant except for the important fact that there is no pain. In particular a little white papilla appears around the injection. After a few minutes, a swelling and bright red coloring occurs. In general, these symptoms are slight and disappear within twenty-four (24) hours. No infection was associated with these injections.

It has been found that a treatment of 10 days with amounts representing the equivalent of 5 to 10 ants (venom sacs or abdomen) during the last 5 days provides substantial relief or disappearance of arthritic symptoms. In an initial series of tests given in Bolivia, relief in many cases appeared to last over a period of years. Furthermore, in each case, no adverse side effects were observed.

Test Results for Utility

Arthritus was simulated in rats for testing the anti-inflammatory properties of the extracted material. In addition, a carefully constructed double-blind test was made on humans. Both tests are described in detail below. This test was limited to human subjects carefully selected so that all had rheumatoid arthritis according to the American Rheumatism Association criteria. Accordingly, it is believed that substantial utility for treatment of rheumatoid arthritis has been demonstrated. It is believed that arthritis of other forms are sufficiently divergent in etiology (non-auto-immune ailments) that no reasonable prediction can be made as to the utility of this invention for treating gouty and other forms of arthritis. However, tests on laboratory animals (set forth below), do indicate that the venom is an anti-inflammatory agent.

Human Study I (Symptomatic Relief Indicia)

To test the potential efficacy of this venom a double-blind clinical trial was undertaken at the Laboratorio Clinico Serrales in Santo Domingo, D.R. This trial was designed by Charles Sisk, M.D., former Director of Medical and Scientific Affairs of the National Arthritic Foundation, and at the time of the test, Associate Professor of Medicine, University of Missouri Medical Center. The principal co-investigator of the study was Harvey Brown, M.D., Professor of Medicine, University of Miami School of Medicine. The trial was conducted during the interval from April 1975 through August 1975.

For the purpose of this study, a Method I extract of venom was used. Venom was extracted manually from abdominal pouches of the insect, mixed with a physiological saline solution, refrigerated with ice, and shipped to the Dominican Republic from Bolivia. No attempt was made to further purify the extract as temperature stability and other physiochemical characteristics were not well defined. It is believed that early attempts to add preservatives to the venom may have resulted in causing the venom mixture to become inactive.

Selection of Subjects—I

Thirty subjects were located who all met the Food and Drug Administration (FDA) definition (1970) of having active rheumatoid arthritis. The FDA definition requires having greater than a defined level of at least three out of four RA parameters as defined by the American Rheumatism Association (ARA) criteria (1958) for rheumatoid arthritis (RA). The four parameters are listed below. The technique for measuring these parameters and the criteria for meeting the FDA definition of RA disease as set forth in FDA and ARA standards was followed.

Thirty-two subjects were found available for study entry but two did not return for treatment so that only thirty were available for the trial.

Prior to study entry all subjects on anti-inflammatory medications were instructed to stop this medication for at least three days before beginning the trial. One criteria established before accepting a subject was that the subject could not be on steroid treatment of over 10 mg. prednison-equivalent during the three-month interval before study entry. No subject had received gold salt treatment before or during the trial.

All subjects were initially randomized to venom-treated and placebo groups in accordance with a double-blind, parallel design. Ten (10) subjects initially randomized to the placebo treatment were subsequently treated with venom thus permitting a crossover comparison of this group.

Procedure—I

Both venom and placebo were administered by subcutaneous injection of the upper arm or thigh. Venom was given in increasing single daily doses over several days until a maximum 1 milliliter (ml) dose was achieved according to the following schedule:

| DAY | DOSE |
|---|---|
| 1 | 0.1 ml |
| 2 | 0.2 ml |
| 3 | 0.3 ml |
| 4 | 0.5 ml |
| 5 | 1.0 ml |
| 6 | 1.0 ml |
| 7 | 1.0 ml |
| 8 | 1.0 ml |
| 9 | 1.0 ml |
| 10 | 1.0 ml |
| 11 | 1.0 ml |
| 12 | 1.0 ml |
| 13 | 1.0 ml |
| 14 | 1.0 ml |

All injections were administered by laboratory personnel not involved in the evaluation of therapeutic response. Subjects were required to come to the Clinic each day for their injections. Compliance was excellent and no subjects deviated from the treatment schedule.

To simulate both the local and systemic effects of the venom, histamine phosphate (0.1 mg. base-equivalent) was given to the placebo group. Although this preparation did not satisfactorily simulate venom effects, precautions were taken to maintain double blindness by covering injection sites during evaluation and by not advising subjects of the types of side effects they might experience from venom or placebo.

All pre-treatment evaluations were performed by one of the co-investigators with three exceptions. The three exceptions were examined by a third rheumatorlogist trained in the United States. All follow-up evaluations were done by one of the co-investigators.

If patients needed supplementary medication during the study they were given propoxphene and instructed to take it on an as needed basis. They were advised to avoid all other anti-rheumatic medication including aspirin and any other aspirin-containing medication.

The four parameters used to determine the existence of active RA were also used to evaluate.

a. number of clinically active joints;

b. Erythrocyte sedimentation rate (ESR), as measured by the Westergren method;

c. duration of morning stiffness; and d. grip strength. Each of the above four parameters is measured as set forth in the ARA Cooperating Clinics Committee Observer's Guide (1958).

The age range of the 16 cases receiving venom was 35 to 71 years with a mean of 58 years and of the 14 cases in the placebo group 34 to 74 years with a mean of 54 years. In the venom treated group there were 14 females and 2 males, in the placebo group, 7 females and 7 males. Functional classification of these therapeutic groups is shown in Table I.

Results—Procedure I

All rheumatological evaualations were done within the week prior to study entry (Pre-Rx), at the termination of the two-week treatment interval (Post-Rx I) and at an interval thereafter (Post-Rx II) which was four weeks after Post-Rx I in the case of some subjects and six weeks in the case of other subjects. The Post-Rx II data, whether taken at four or six weeks after treatment, is combined in the following analysis. The data is summarized in Table II for the parallel venom and placebo groups. Table III is extracted from Table II and provides a summary of the significantly improved parameters. The data indicates that statistically significant improvements occur in grip strength and in the number of clinically active joints in the venom treated group while corresponding improvement does not occur within the placebo treated group.

No adverse reactions other than local ones were observed in subjects receiving venom. All subjects received a battery of laboratory tests including tests for toxicity. These included, pre- and post-treatment CBC, urinalysis, clinical chemistries (SMA-12). None of these parameters suggested any hemotologic, renal, hepatic or other toxicity. Local reactions consisted of marked induration, heat and erythema at the points of injection. Most of these reactions subsided spontanteously in one or two weeks after discontinuing treatment.

One subject developed a localized abscess. This responded promptly to antibiotic therapy.

To confirm that the present invention therapeutic agent did not obtain its therapeutic properties by acting as a stress agent and stimulating endogenous cortisol product, pre- and post-treatment serum cortisol levels were measured in all cases. No differences of before and after therapy hormone level were observed. This result indicates that the dangerous condition known as "adrenal crisis," which is caused by repeated stimulation of the adrenal glands, is not likely to occur as a result of extended treatment according to the present invention.

To assess the possibility of serious allergic reactions occuring when individuals were re-treated, four subjects from the venom group were selected for a second complete, two weeks of treatment following the same dosage schedule as originally. Again observations were made to determine allergic response. Moderate local reactions noted in these subjects when initially treated were absent on re-treatment and all four subjects appeared to have a better therapeutic response than they did on the original trial. This second treatment was initiated two months after termination of the first treatment.

The mean values of the various rheumatological parameter measured during the trial are set forth in Table II. The statistically significant mean values together with their standard deviations are set forth in Table III.

It might be noted that the improvement obtained was not obtained immediately at the termination of the injections or, at least, the improvement obtained by that time was not statistically significant. The statistically significant improvement was observed at the end of a four or six week period (Post-Rx II) after termination of the injections. Apparently, it takes time for the inflammation to subside and for the body to adjust to the change. It is not yet known for how long the treatment is effective or, more specifically, what the relationship is between time after treatment and level of return of symptoms to pretreatment levels.

The extent of improvement in the number of clinically active joints is a measure of the number of joints which at Pre-Rx were degrees 2, 3 or 4 on the ARA definition of degree of involvement of clinically active joints and which became grades zero or one at Post-Rx II. Thus the improvement had to pass over the threshold between degrees 2 and degree 1 in order for it to be recorded as an improvement in the data set forth in the tables. A joint which improved from a fourth degree level (severe) to the second degree level (minimal—definitely present, but mild) under the ARA definitions would not be reflected as an improvement in the data in the tables. It is believed that the extent of the improvement obtained by this treatment and its statistical significance would be increased if the analysis took into account all improvement and not just the improvement that passed the threshold between degrees two and one.

With respect to Table II, it should be noted that the footnoted P levels were made with the appropriate parametric "t" tests for grip strength and for number of clinically active joints.

Ten of the fourteen individuals in the placebo group were given the venom treatment after termination of the parallel venom and placebo trial. The individuals selected were not selected at random but were those who tended to have the worst symptoms. Thus the results of this crossover trial group cannot be rigorously statistically analyzed. Nonetheless, there was a reduction of number of clinically active joints in the groups of ten subjects from a Pre-Rx mean of 23.9 (std. dev. 12.9) to a post treatment mean of 13.0 (std. dev. 11.9). This suggests a statistically significant difference at the P 0.05 level. The other rheumatological parameters of this cross-over group did not show a statistically significant degree of improvement.

TABLE I

| ARA Functional Class* | Number In Class | |
|---|---|---|
| | Venom Group | Placebo Group |
| 1 (No handicap) | 0 | 0 |
| 2 (discomfort or limited motion) | 5 | 7 |
| 3 (limited self care) | 8 | 5 |
| 4 (incapacitated) | 3 | 2 |
| | 16 | 14 |

*The class definitions are set out more fully in the Observer's Guide issued by the ARA Cooperating Clinic's Committee.

TABLE II

Mean Values Of Rheumatologic Parameter Measurements For Venom-Treated And Placebo Groups

| Group | Parameter | Mean Measurement Value | | |
|---|---|---|---|---|
| | | Pre-Rx$^a$ | Post-RxI$^b$ | Post-RxII$^c$ |
| "VENOM" (N = 16) | Grip strength: | | | |
| | (mm of Hg) Right Hand | 92.0 | 104.0 | 177.0 |
| | Left Hand | 63.8 | 74.3 | 181.0 |
| | Morning stiffness (duration in hours) | 2.8 | 2.5 | 2.2 |
| | E.S.R; Westergren Method (mms of sed. per hr.) | 56.9 | 65.4 | * |
| | Active joints$^d$ (number of) | 19.6 | 17.3 | 8.6 |
| "PLACEBO" (N = 14) | Grip strength: | | | |
| | (mm of Hg) Right Hand | 99.5 | 103.7 | 102.3 |
| | Left Hand | 105.6 | 114.2 | 125.3 |
| | Morning stiffness (duration in hours) | 3.4 | 3.1 | 3.0 |
| | E.S.R; Westergren Method (mms of sed. per hr.) | 63.1 | * | * |
| | Active joints$^d$ (number of) | 24.0 | 19.5 | 15.4 |

*Insufficient Data
$^a$data taken within the week prior to study entry
$^b$data taken at termination of the two week treatment interval
$^c$data taken at four or six weeks after termination of treatment
$^d$ARA criteria for degrees of involvement were used; specifically finger joints meeting the ARA definition for degrees 2, 3 or 4 were considered clinically active. The values listed in the Table are the mean number of clinically active joints for the group.

TABLE III

Statistically Significant RA Parameter Measurements

| Group | Parameter | Pre-RX Mean & Std. Dev. | Post-Rx II Mean & Std. Dev. |
|---|---|---|---|
| "VENOM" (N = 16) | Grip strength: Right Hand$^c$ | 92.0 (56.9)$^a$ | 177.0 (56.6)$^b$ |
| | | 63.8 (26.8)$^a$ | 181.0 (48.7)$^b$ |
| | Active joints$^g$ | 19.6 (10.7)$^e$ | 8.6 (5.0)$^f$ |

TABLE III-continued

Statistically Significant RA Parameter Measurements

| Group | Parameter | Pre-RX Mean & Std. Dev. | Post-Rx II Mean & Std. Dev. |
|---|---|---|---|
| | number strength: active joints, Hand | 99.5 (51.6)[a] | 102.3 (58.0)[b] |
| "PLACEBO" (N = 14) | Left Hand | 105.6 (62.8)[a] | 125.3 (58.4)[b] |
| | Active joints | 24.0 (13.8)[e] | 15.4 (19.6)[f] |

[a] For grip strength, a comparison of the means of the venom and placebo groups Pre-Rx shows arise by significant difference.
[b] For grip strength, a comparison of the means of the venom and placebo groups Post-Rx II shows a statisically significant difference; specifically a difference that could arise by chance less often than once in twenty trials (P at .05 level).
[c] For right hand grip strength in the venom group alone, a comparison of the means between Pre-Rx and Post-Rx II values shows a statistically significant difference; specifically a difference that could arise by chance less often once in one hundred trials (P at .01 level).
[d] For left hand grip strength in the venom group alone, a comparison of the means between Pre-Rx and Post Rx II values shows a statistically significant difference; specifically a difference that could arise by chance less often than once in two hundred trials (P at .005 level).
[e] For number of clinically active joints, a comparison of the means of the venom and placebo groups Pre-Rx shows no siginificant statistical difference.
[f] For number of clinically active joints, a comparison of the means of the venom and placebo groups Post-Rx II shows a statistically significant difference; specifically a difference that could arise by chance less often than once in twenty trials (P at .05 level).
[e] For number of clinically active joints in the venom group alone, a comparison of the means between Pre-Rx and Post-Rx II values shows a statistically significant difference; specifically a difference that could arise by chance less often than once in one hundred trials (P at .01 level).

Utility as an Anti-Inflammatory Agent for Simulated Rheumatoid Arthritis in Rats and Experiments to Indicate Methods for Enhancing Effectiveness of the Subject Invention Extract The following is a report of tests utilizing rats to show the general anti-inflammatory properties of the subject invention extract and methods for further purifying or using said extract to enhance its effectiveness.

Rheumatoid arthritis was simulated in Sprague—Dolly rats by injecting an adjuvant, Parrigan—C, into the right foot pad of the rat. Measurements were made along the dorsal ventral axis in millimeters. The untreated left foot was also measured as a standard, and is reported in parenthesis in the following Tables.

It should be pointed out that although these tests are generally considered to simulate rheumatoid arthritis closely enough for the test results to be, at least, an indication of the effectiveness of the material being used for use in human beings, the tests in fact generally indicate the anti-inflammatory properties of the material being tested. As will be seen in data presented below in a different test series, the subject invention extract not only reduces rheumatoid arthritis symptoms but also reduces the measured RA factor in the blood, and apparently accomplishes these results without increasing the cortisol serum levels in the blood.

PREPARATION OF EXTRACT FOR TESTS

With reference to Table IV, in general, the data shown in Column A are the results of untreated simulated arthritis Column B shows the results of treatments using I.P. injections (similar to intravenous in humans) of the Therapeutic Agent extracted by Method I (supra).

The Therapeutic Agent utilized for obtaining both the results shown in Columns C and D, was a method I extract filtered through an 0.45μnalge filter before use. However, the material used for the results in Column D was heated to about 37° C. before filtration to increase the yield.

Column E shows the results of a regular multiple daily injections, while Column F shows the results of a particular variation, as set forth in the table.

Empirical conclusions which can be drawn from Table IV include the possible increased efficiency obtainable by utilizing intra-peritoneal (I.P.) injections which indicates that intravenous possibly could be utilized in human studies. Additionally, apparently increasing the filtration step yield by heating the Therapeutic Agent before filtration does not decrease the effectiveness of the agent and may actually give increased efficacy over the agent which is filtered without heating. Finally, multiple daily injections appear to give faster and greater relief.

The data in Table V indicate that a daily injection (Column B) is more effective than injections on a less often schedule. Column C shows results of injection every other day. Column A shows the results of one injection only. Column D is the control.

The data in Table VI confirm the conclusions set forth above with respect to multiple daily injects and that a handling technique wherein the filtered therapeutic agent is stored at −70° C. will, when thawed, still be a viable therapeutic agent.

TABLE IV

| Day | A | B | C | D | E | F |
|---|---|---|---|---|---|---|
| 1 | 10.6 (4.5) | 8.7 (4.5) | 9.5 (4.0) | 8.3 (4.5) | 8.5 (4.5) | |
| 2 | 11.1 (4.5) | 8.7 (5.0) | 9.8 (4.5) | 8.1 (4.5) | 8.2 (5.0) | |
| 3 | 11.8 (5.0) | 9.2 (5.0) | 9.6 (4.5) | 9.1 (4.5) | 8.0 (5.0) | |
| 4 | 11.4 (5.0) | 8.3 (5.0) | 10.0 (4.5) | 9.1 (4.5) | 7.7 (?) | |
| 5 | 10.8 (4.5) | 7.7 (5.0) | 9.6 (4.5) | 8.0 (4.5) | 7.0 (5.0) | 9.5 |

| | Number of Rats Tested | Material Injected into Right Food Pad |
|---|---|---|
| A | 5 | 0.03 ml. adjuvant + 0.5 ml. saline solution |
| B | 5 | 0.03 ml. adjuvant + 0.5 ml. extract unfiltered (I.P. once a day) |
| C | 5 | 0.03 ml. adjuvant + 0.5 ml. extract filtered 0.45μ Nalge (I.P. once a day) |
| D | 5 | 0.03 ml. adjuvant + 0.5 ml. extract warmed to about37° C. before filtering through 0.45μ Nalge (I.P. once a day) |
| E | 3 | 0.03 ml. adjuvant + 0.3 ml. extract (I.P. 3× a day) |
| F | 2 | Injection with 0.5 ml. extract I.P. for 2 days, thereafter 0.03 ml. adjuvant + 0.5 ml. extract I.P. every day |

TABLE V

| A | B | C | D |
|---|---|---|---|

TABLE V-continued

| Day | (1 ml. extract first day only) | (1 ml. extract every other day) | (1 ml. extract every day) | (1 ml. saline every day) |
|---|---|---|---|---|
| 1 | 8.9 ± 0.418 (4.5) | 8.5 ± 0.740 (4.5) | 8.4 ± 0.964 (4.5) | 9.9 ± 0.823 |
| 2 | 11.0 ± 0.446 (4.5) | 10.1 ± 0.374 (5.5) | 9.5 ± 0.706 | 10.9 ± 0.349 |
| 3 | 13.1 ± 1.28 (5.5) | 11.4 ± 0.582 (5.0) | 10.3 ± 0.978 (6.5) | 12.0 ± 0.893 |
| 4 | 13.1 ± 1.18 | 11.5 ± 1.09 (5.0) | 10.1 ± 1.11 (6.0) | 12.7 ± 0.982 |
| 5 | 12.6 ± 1.39 (5.0) | 10.8 ± 1.2 (5.0) | 9.3 ± 14 (6.0) | 12.4 ± 0.968 |
| 6 | 12.3 ± 1.07 (5.0) | 10.2 ± 1.16 (5.0) | 9.2 ± 1.36 (5.0) | 12.4 ± 0.582 |
| 7 | 12.0 ± 1.07 (6.0) | 9.8 ± 0.747 (5.5) | 9.1 ± 1.32 (6.0) | 11.4 ± 0.374 |
| 8 | 11.8 ± 0.929 (5.0) | 9.9 ± 1.35 (5.0) | 8.9 ± 1.9 (5.0) | 11.6 ± 0.374 |

| | Number of Rats Tested | Material Injected into Right Foot Pad |
|---|---|---|
| A | 5 | 0.03 ml. (?) using 30G needle, followed by a total of 1.0 ml. of extract subcutaneously injected in 2 sites in back, of 0.5 ml. each site, 25G needle used for extract injections. |
| B | 5 | Same as A, but will receive 1 ml. of extract every other day for 14 days for a total of 7 ml. of extract per rat. |
| C | 5 | Same as above, but will receive 1 ml. every day for 14 days. |
| D | 5 | Same as above, but will receive saline solution every day for 14 days. Note; 1.5 ml. saline (I.P.) was injected in 1 rat, 2 others were injected with 1 ml. (I.P.). |

TABLE VI

| Day | Saline | Venom I | Venom II | Venom III | Venom IV |
|---|---|---|---|---|---|
| 2 | | | | | |
| 3 | | | | | |
| 4 | | | | | |
| 5 | 13.0 (4.5) | 8.5 | 8.0 | 8.5 | 5.5 |

This table shows the results of a handling technique followed by multiple injections over a short period of time. The data appears to indicate that multiple I.P. injections utilizing carefully prepared material will give enhanced effectiveness for the treatment. The measurements were taken on the fifth day only and are the results of the following experiments:

Day 1 about 130 ml. of extract prepared as described above were concentrated to 34 ml. and filtered using an amicon UM-2 membrane. The result being material was frozen at −70° C.

Day 3 venom thawed and maintained on ice for the entire experiment. Five rats were injected with adjuvant (described above). One rat was injected I.P. with 1 ml. of saline, the other with the prepare abstract at about 2 p.m. and again at 9:30 p.m.

Day 4 1 ml. of venom or saline was injected at about 9:30 a.m. followed bya second injection at 2 p.m.

Day 5 1 ml. of venom or saline was injected at about 9:30 a.m. followed by a second injection at 1 p.m.

Human Study II (Blood Analysis Indicia—RA factor; Complement System)

Extraction of Agent
Method I (Aqueous Extraction-Supra)
Subject I-A

The subject is a 54 year old woman with a 4 year history of mixed cryoglobulinemia characterized by severe arthralgias, weakness and purpura. Her Rheumatoid Factor (RA) titer was $40 \times 10^3$ units. She tolerated corticosteroids and chlorambucil poorly and had been undergoing frequent plasmapheresis for relief of symptoms. Since her purified IgG-IgM cryoglobulin activated serum C in-vitro, a trial of ant venom was proposed and her informed consent obtained.

She was treated with a two-week course of daily i.d. injections of venom. In addition to clinical evaluation, her immunoglobulins (Ig), cryoglobulin, C3, C4 (Complement System), and RA were evaluated.

Results I-A

Within one week during treatment, her condition markedly improved with alleviation of arthralgias. For six months she has remained in clinical remission.

Her Ig levels have not changed, but the cryoglobulin decreased four-fold in concentration. *Her RA titer decreased to* $5 \times 10^3$ *units.* Serum C3 levels have increased 33-fold, and C4 levels 1.4-fold, but the latter remains below normal. She has not required plasmapheresis.

Subject II-A

One women volunteer was tested for RA factor before and after treatment with injections of the Therapeutic Agent according to the present invention which lasted three weeks.

Results II-A

She initially had a positive RA factor test. After three weeks her RA factor test indicated negative.

Note: It was observed that patients suffering from asthma experienced a remission of symptoms coincidently with their treatment with the Therapeutic Agent. Thirteen patients exhibiting symptoms of asthma were treated with injections as described herein. Eleven showed marked improvement.

Purification and Identification of the Active (Therapeutic) Agent

The following purification methods and tests were devised and run by Dr. Duane R. Schultz and Patricia I. Arnold, Department of Medicine, Division of Immunology, University of Miami, School of Medicine, Miami, Florida. As noted above, for convenience and in view of the above investigations, the effect of the active agent on the human complement system was chosen as a principal assay method for the active agent. Actual testing on humans and rats was also accomplished to confirm the viability of this assay method.

It should be noted that these studies were run on the material subsequent to, and as a result of, the prior observations and conclusions drawn by Gunter Holzmann, that the venom is efficacious for the treatment of rheumatoid arthritis.

PURIFICATION OF POLYSACCHARIDE FOR CLINICAL STUDIES

Method I-A (First Purification Method)

Starting with X ml of extract (Method I (above)) (usually 47 ml, 0.275 mg protein/ml): 9 parts of absolute ethanol are slowly added to 1 part of the extract with constant stirring at 0° C., the mixture is stirred for 1 hr. at 0° C., and centrifuged (Sorval RC2-B, 12,000×g, 30 min, 4° C.). The supernatant fluid is discarded, and the precipitate is washed one time with 90 percent ethanol at 0° C. and centrifuged. A small volume of distilled water is added to suspend the material, and it is lyophilized to eliminate the alcohol. Distilled water is added to dissolve the dry powder, it is centrifuged to eliminate insoluble material, and the supernatant fluid is dialyzed vs. 0.018 M sodium phosphate containing 0.15 M NaCl, pH 7.2 (PBS). This preparation, which is mostly polysaccharide but contains at least one protein as shown by polyacrylamide gel electrophoresis, may be stored in the lyophilized state, and is reconstituted by adding the desired volume of distilled water.

Method I-B (Second Purification Method)

The preparation above from Method I is applied to a column containing Concanavalin A linked to Sepharose (Pharmacia Fine Chemicals, Uppsala, Sweden). The column varies in size, depending on the volume of material from Method I. With 47 ml of material from Method I, the column size is 2.4×22 cm. The Sepharose-Concanavalin A is equilibrated with PBS at 25° C. After application, the column is thoroughly washed with 0.3 M sodium borate buffer, pH 8.7, and the highly purified polysaccharide is eluted with 0.1 M α-methyl-D-mannoside in PBS. The polysaccharide is dialyzed vs. PBS and stored in the lyophilized state at 4° C.

Method IV (Third Purification Method)

The extract (Method I (above)) is filtered through a ultrafiltration membrane at 4° C. (Amicon$^R$ Corp., Lexington, Mass.). A PM-10 membrane with a cut-off M.W. of ca. 10,000 daltons is used. The ultrafiltrate, which contains heat-stable factor (polysaccharide) and heat-labile factor (trypsin-like enzyme), is concentrated further to an appropriate volume with an Amicon UM-2 membrane. This preparation may be stored in the lyophilized state at 4° C.

DISCUSSION OF PURIFICATION METHODS
Method I-A (Human Testing)

The active agent purified utilizing this method has been tested on four human patients with rheumatoid arthritis by injection of the agent into the patient. In general, it appeared to require somewhat more time before the patient showed a remission of symptoms. Remission occurred after the 11th–13th injection. It is noted that all patients had rheumatoid arthritis for an extended period of time and the cases were rather severe. One of the patients had chronic asthma and this ailment also showed a remission of symptoms during treatment.

It is concluded that material purified according to Method I-A must either be utilized over an extended period of time or the preparation will need to be more highly concentrated.

Method I-B

This is simply a refining and cleaning up of the polysaccharide material obtained in Method II by repeating the steps.

Method I-C

This has been used with success in treating rats with adjuvant induced arthritis according to the procedures discussed in detail above.

IDENTIFICATION OF THE ACTIVE AGENT

Initial Testing and Discussion: Complement System as Indicia of Active Agent

This analysis is of a polysaccharide which appears to be an active factor in the therapeutic agent of the present invention.

The polysaccharide (PS) from the venom of a tropical ant interacts with a human mono-immunoglobulin protein(s) in serum, causing C1 activation and the consumption of the functional activity of C4 and C2.

The PS had a heterogenous size in native ant venom. The smallest moiety that activated serum C1 had a MW of ca. 3,000 daltons as determined by gel chromatography. The PS was not precipitated by barium salts, showing no apparent sulfate groups. The following sugars and the molar ratios were found by gas chromatography: mannose (7.7), fucose (1.8), N-acetylgalactosamine (1.6), galactose (1.4), glucose (1.0), and N-acetylglucosamine (1.0).

Evidence showing that a serum beta-lipoprotein (B-LP) participates with venom PS to cause activation of C1 includes: 1) The PS caused a visible precipitation when incubated with normal human serum or its highly purified B-LP at 37C for 12 hours. The B-LP was depleted from the supernatent of serum when the precipitate caused by the PS was removed by centrifugation; 2) The B-PL in PS-treated serum was heavier than the PS or the B-LP alone in sucrose density gradients. Both 0.01 M EDTA and 0.3 M NaCl prevented the interaction of the PS and the B-LP; 3) the B-LP-PS complexes increased in mobility after electrophoresis in agarose. However, these complexes did not appear to bind $^{125}$I-Clq as tested by standard procedures for detecting immume complexes.

CONCLUSION

These studies confirm that the ant venom PS activates the classical complement pathway, probably first by an ionic binding to a B-LP, which then causes activation of C1.

To further confirm the effects of factors in the extracted "Venom" on the complement system, and thereby their usefulness in alleviating auto-immune ailment symptoms, further studies were also done by Dr. Duane R. Schultz and Patricia I. Arnold, Department of Medicine, Division of Immunology, University of Miami, School of Medicine, Miami, Florida 33101, on extract obtained according to method I (above).

The results of the various studies are summarized in the following tables wherein the ant venom used was essentially an extract according to Method I.

TABLE I

Summary of the characteristics and the anti-complementary action of two factors in ant venom (Pseudomyrmex sp.) (11).

| Characteristics of Native Ant Venom | Action |
|---|---|
| In human serum, in vitro. | Causes activation/inactivation of C1, C4, C2, C3b INA, C3, factor B. Has no effect on C1 INA, C5, C8, C9. |
| On human purified C components. | Inactivates C2, C3b INA. Has no effect on C3, C4. |
| Physical-chemical | Factor 1: resistant to boiling, active in pH ranges of 5 to 9, temperature-dependent, resistant to protease inactivator phenylmethylsulfonylfluoride (pmsf). Mechanism of action in serum inhibited by EDTA; activates C1 in |

TABLE I-continued

Summary of the characteristics and the anti-complementary action of two factors in ant venom (Pseudomyrmex sp.) (11).

| Characteristics of Native Ant Venom | Action |
|---|---|
| | classic C pathway resulting in C4 and C2 inactivation; causes inactivation of C3 in alternative C pathway. |
| | Factor 2: heat-labile (inactivated in 30 min, 56° C.), temperature-dependent, inhibited by natural inhibitors in serum, inactivated by pmsf, not inhibited by EDTA. Acts directly on C components. |

TABLE II

Boiling native ant venom to determine its effect on the functional activity of C4 in normal human serum after incubation for 1 hr at 37° C.

| Incubation of Serum With | Boiling Time[a] (Min) | C4 (Percent Loss)[b] |
|---|---|---|
| | 0 | 98 |
| | 5 | 98 |
| Boiled | 30 | 96 |
| Ant Venom | 60 | 84 |
| | 120 | 84 |
| Buffer | 120 | 20 |

[a]Venom was boiled prior to incubation with serum or buffer.

[b]Percent loss $= 1 - \dfrac{CH_{50} \text{ units/ml at 1 hr}}{CH_{50} \text{ units/ml at 0 hr}} \times 100$

TABLE III

Effect of concentrated boiled or unboiled ant venom ultrafiltrate on the functional activity of C4 in serum, purified C4, purified C2, and purified C3 after incubation for 4 hr at 37° C. The ultrafiltrate of ant venom from a Diaflo[R] PM-10 membrane was concentrated with a Diaflo[R] UM-2 membrane.

| | | Complement Component Titer ($CH_{50}$ units/ml) | | | |
|---|---|---|---|---|---|
| | | C4 in | Purified | | |
| Reactant | Boiled[b] | Serum | C4 | C2 | C3 |
| Concentrated Ultrafiltrate[a] | + | 12,000 | 6,000 | 4,000 | 7000 |
| | − | 400 | 500 | <2 | 2 |
| Buffer | + | 250,000 | 6,000 | 3,500 | 7,000 |
| Control | − | 250,000 | 6,000 | 3,500 | 7,000 |

[a]Concentration of Diaflo[R] PM-10 membrane ultrafiltrate (molecular weight ca. ≦10,000 daltons) with Diaflo[R] UM-2 membrane (molecular weight cut-off is ca. 1,000 daltons (26).
[b]Boiled 5 min.

TABLE IV

Effect of concentrated boiled or unboiled ant venom pools 1 and 2 and their unboiled ultrafiltrates from the Ultrogel column of FIG. 2 on the functional activity of C4 in serum and on purified C4, after incubation for 4 hr at 37° C.

| Column Pool | Approximate Molecular Weight (Daltons) | Condition | C4 ($CH_{50}$ units/ml $\times 10^2$) Serum | Purified |
|---|---|---|---|---|
| 1 | 175,000 | Boiled[a] | 200 | 64 |
| | | Not Boiled | 250 | 1.5 |
| | | Ultrafiltrate[b] | 300 | 10 |
| 2 | 32,500 | Boiled | 1,000 | 64 |
| | | Not Boiled | 1,000 | 15 |
| | | Ultrafiltrate | 70 | 16 |
| Buffer Control | — | Boiled | 1,000 | 65 |
| | | Not Boiled | 1,000 | 65 |
| | | Ultrafiltrate | 1,000 | 65 |

[a]Boiled 5 min.
[b]Ultrafiltrate of Diaflo[R] PM-10 membrane (molecular weight cut-off is ca. 10,000 daltons (26).

TABLE V

Effect of native ant venom or an eluate of the venom from polyacrylamide gels on purified human C3 and C4 after incubation for 2 hr at 37° C.

| Conditions with Ant Venom | $CH_{50}$ Units/ml | |
|---|---|---|
| | C3 | C4 |
| Unfractionated[a] | 10,000 | 30,500 |
| Eluate from gel | <4 | 3,000 |
| Buffer control | 11,000 | 30,500 |

[a]Final concentration, 1 mg/ml.

TABLE VI

Incubation of ant venom with a 40 percent ammonium sulfate (A.S.) fraction or the supernatant fluid of normal human serum (NHS). After each mixture was treated with a final concentration of 0.5 mM phenylmethylsulfonylfluoride and dialyzed, they were then incubated with unfractionated NHS for 2 hr at 37° C, and the activities of C4, C2, and C3 were tested by hemolytic assays

| Reactant with NHS | Complement Component Titer in Serum ($CH_{50}$ Units/ml $\times 10^2$S) | | |
|---|---|---|---|
| | C4 | C2 | C3 |
| 40% A.S. Fraction + Venom | 350 | 17 | 60 |
| 40 % A.S. Fraction + Buffer | 2,500 | 250 | 240 |
| 40 % A.S. Super + Venom | 450 | 30 | 60 |
| 40 % A.S. Super. + Buffer | 2,500 | 230 | 240 |
| Buffer + Venom | 325 | 17 | 60 |
| Buffer + Buffer | 2,500 | 250 | 240 |

TABLE VII

Titers of C4 and C2 in normal human serum incubated with a washed precipitate consisting of ant venom and normal human serum factors. The mixture, and a control with no precipitate, were incubated for 4 hr at 37° C.

| Reactant | $CH_{50}$ Units/ml | |
|---|---|---|
| | C4 | C2 |
| Serum + precipitate | 100 | 50 |
| Serum | 450,000 | 25,500 |

In view of the studies outlined in the tables above, the following identification scheme was devised and applied to the venom extract.

IDENTIFICATION OF THE ACTIVE FACTOR

The active factor of the present invention was isolated and the isolated material characterized by electrophoresis separation of components followed by reactions with various known reagents; elemental analysis; IR spectrometry; and solubility; all as set forth below:

ISOLATION OF THE POLYSACCHARIDE IN NATIVE ANT VENOM

Figure 1:
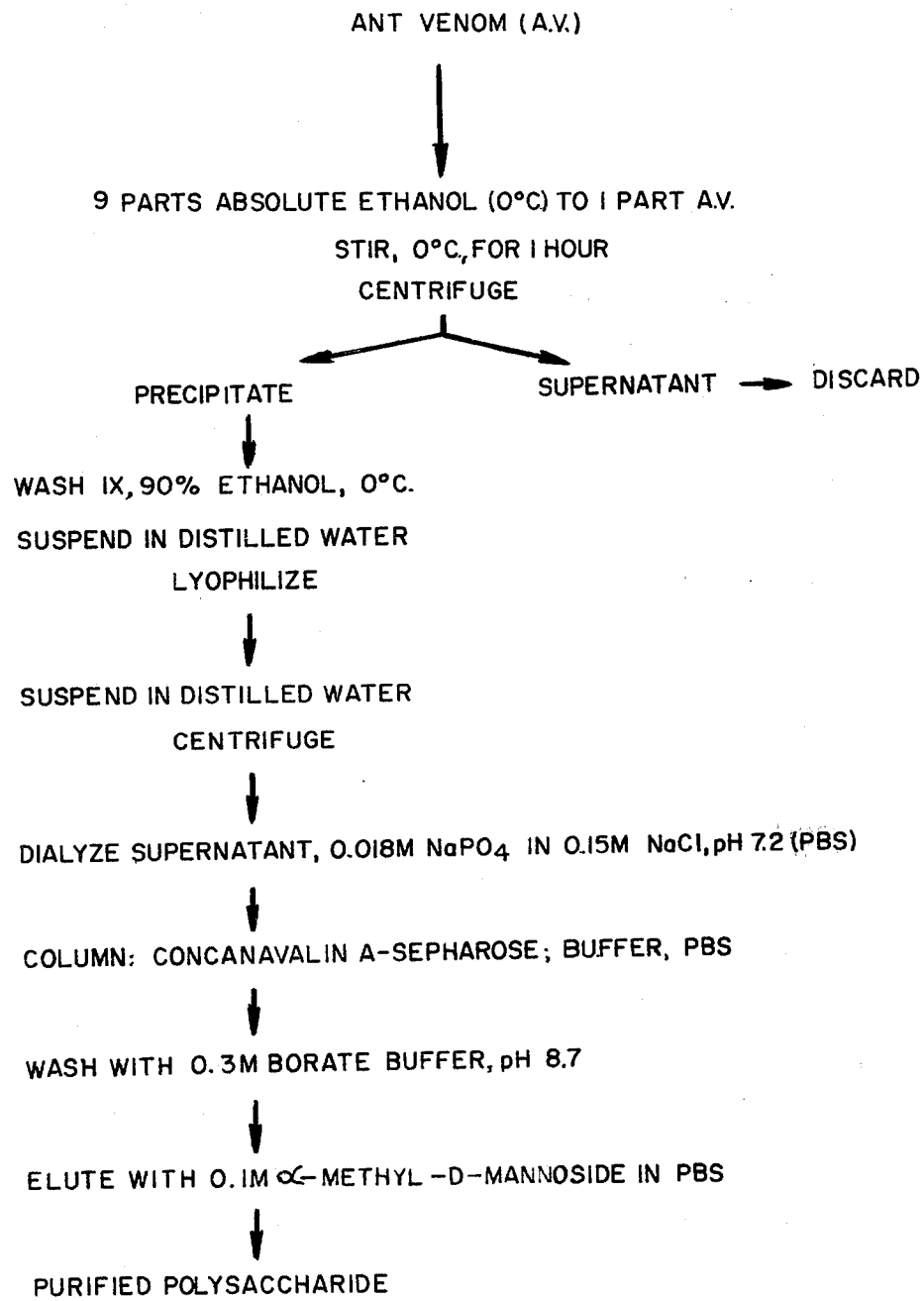
FIG. 1 is a flow diagram for the purification of Polysaccharide from native ant venom (extract by Method I).

Nine parts of absolute ethanol were slowly added to 1 part of the venom (47 ml of venom, 0.275 mg protein/ml, 180 µg/ml of uronic acid) with constant stirring at 0° C. A light precipitate formed, the mixture was stirred for 1 hr at 0° C., and centrifuged (Sorvall RC2-B; 12,000×g; 30 min; 4° C.). The supernatant fluid was discarded because after evaporation of the alcohol and solubilization in an aqueous buffer, the product did not cause C4 consumption in normal human serum*. The precipitate was washed one time with 90 percent ethanol at 0° C. and centrifuged. A small volume of distilled water was added to suspend the material, and it was lyophilized to eliminate the alcohol. Forty-seven milliliters of distilled water were added to dissolve the dry powder, it was centrifuged to eliminate insoluble material, and the supernatant fluid was dialyzed against 18 mM sodium phosphate containing 150 mM NaCl, pH 7.2 (PBS). Forty-six milliliters (18 µg/ml of uronic acid) were applied to a 2.4×22 cm column containing Sepharose-Con A that was equilibrated with PBS at 25° C. The column was first washed with PBS, and the latter (300 ml) was concentrated to 46 ml (7 µg/ml of uronic acid) with an Amicon UM-2 membrane (Amicon Corp., Lexington, Mass.). Then the column was thoroughly washed with 300 ml of 300 mM sodium borate buffer, pH 8.7 (no uronic acid recovered), and eluted with 300 ml of 100 mM α-methyl-D-mannoside in PBS. This was concentrated to 46 ml with an Amicon UM-2 membrane, and contained 10.5 µg/ml of uronic acid. All the above pools were concentrated with an Amicon UM-2 membrane to 10 ml at 4° C.

*The polysaccharide causes the activation of the first component of complement (C1) in normal human serum, which in turn acts on its two natural substrates C4 and C2. Thus, C4 and/or C2 consumption indirectly shows that C1 was activated.

POLYACRYLAMIDE GEL ELECTROPHORESIS

The method for polyacrylamide gel electrophoresis using no stacking gel and 7 percent separating gel (Orstein, 1964) (Davis, 1964) is described in the manual of Canalco Co. (Rockville, MD). Gels were stained for protein with Amido Black 10B (Greenfield et al, 1971), and for glycoprotein and polysaccharide with periodic acid Schiff reagent (Segrest & Jackson, 1972). Neutral sugars were detected with anthrone reagent (Seifter et al, 1950), hexuronic acids by the carbazole method of Bitter and Muir (1962), and phosphate by the method of Ames and Dubin (1960).

GAS CHROMATOGRAPHY

To anthrone and uronic acid positive samples was added a final concentration of 3 N HCl, and they were hydrolyzed at 100° C. for 3 hr. The hydrolysates were reduced by sodium borohydride, acetylated with acetic anhydride by standard procedures (Griggs et al, 1971), and the alditol acetates were analyzed by gas chromatography with a Hewlett-Packard apparatus.

Figure 2:
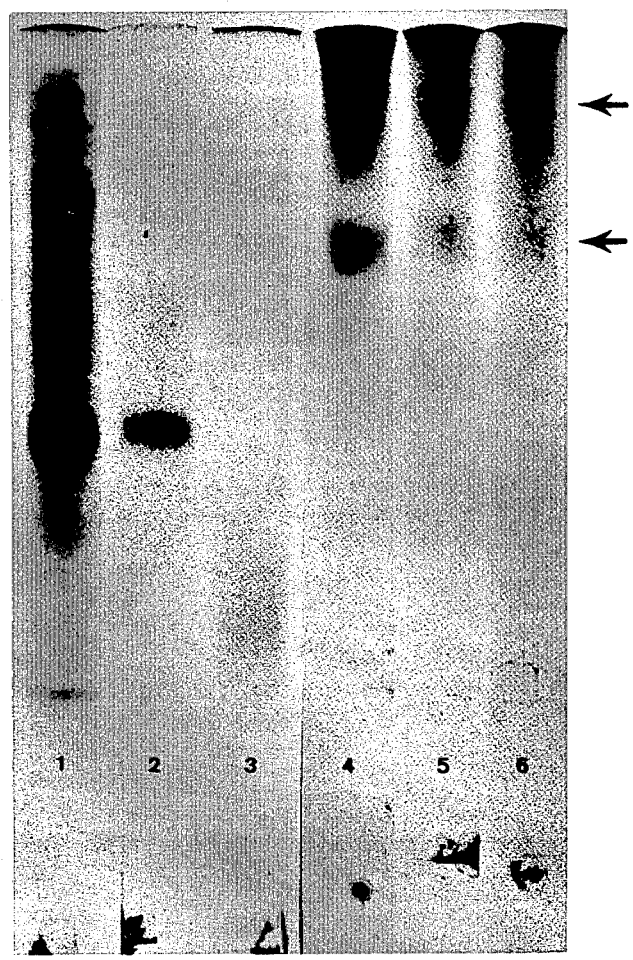
FIG. 2. Analysis of the products of the isolation steps for the ant venom polysaccharide, by disc electrophoresis on polyacrylamide gels. The gels are (1) native ant venom (0.275 mg protein/ml, 180 ng/ml of uronic acid), (2) the alcohol precipitate (lyophilized and solubilized in distilled water, 18 ug/ml of uronic acid), and (3) the product that eluted from the Sepharose-Con A (10.5 ug/ml of uronic acid), all stained for proteins with Amido Black 10B. Gel nos. 4, 5, and 6 are the same products as 1, 2, and 3, but stained with periodic acid Schiff reagent. The arrows point to the polysaccharide(s) which caused C1 activation and C4 and C2 consumption in serum.

The products of the purification steps were subjected to electrophoresis on polyacrylamide gels, applying 250 µl/gel. In FIG. 2, gel columns no. 1, 2, and 3 are, respectively: native ant venom, the alcohol precipitate that was lyophilized and solubilized in distilled water, and the product that eluted from the Con-A column. They were stained with Amido Black 10B. Gel columns no. 4, 5, and 6 are the same as 1, 2, and 3, but they were stained with periodic acid Schiff reagent (PAS). Most of the venom protein was eliminated by the alcohol precipitation step (gel no. 2). The product that eluted from the Con-A column had no detectable protein (gel no. 3), but contained material that did not enter the gel, and at least 2 diffuse bands which stained with the PAS (gel no. 6), indicating a polysaccharide(s).

Serial slices of varying thickness from top to bottom (Table 1) of 6 unstained gels containing the Con-A eluate were pooled, eluted 48 hr with 2 ml of DGVB++ at 4° C., and concentrated with 0.5 ml with an Amicon UM-2 membrane at 4° C. Equal volumes of each concentrated eluate and normal human serum were incubated at 37° C. for 4 hr, and the C4 levels were determined by functional hemolytic assays. Table 1 shows that the product that consumed serum C4 (i.e., activated C1) was in the top 1 to 3 mm, including a portion that did not enter the gel, and also the activity was associated with a second PAS-positive band that entered the gel. Some activity was found between the two major PAS-positive bands which entered the gel, probably indicating that variable quantities of the polysaccharide(s) did not migrate as a homogeneous band.

FRACTIONATION AND CHARACTERIZATION OF THE POLYSACCHARIDE IN NATIVE ANT VENOM

Figure 3A:
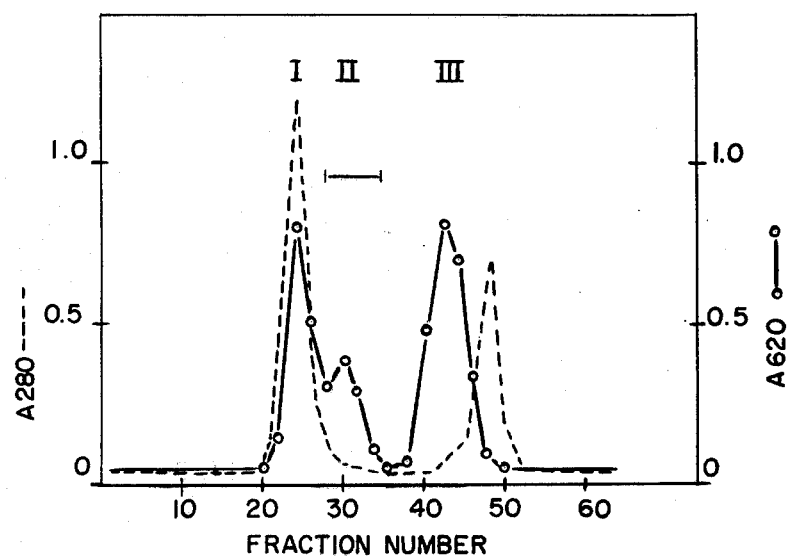
FIG. 3(A). Elution profile of native ant venom (13.8 mg protein/ml) on Sephadex G-25 at 4° C. Fractions were assayed for protein by absorbance at 280 nm and for sugars with anthrone reagent at 620 nm. Of the 3 anthrone-positive peaks, only I and II caused C4 consumption in normal human serum.

One-hundred milliliters of venom were concentrated to 2 ml by ultrafiltration with an Amicon UM-2membrane (13.8 mg protein/ml) at 4° C. and applied to a 1.1×70 cm column containing Sephadex G-25 equilibrated with 5 mM sodium phosphate, 150 mM NaCl, pH 7.5, at 4° C. Individual fractions were assayed for protein by measuring absorbance at 280 nm, for sugars with anthrone reagent, and for the capability to cause consumption of serum C4 by functional hemolytic assays. For the latter, equal volumes of normal human serum and the column fraction were incubated for 4 hr at 37° C., and the titer of C4 was determined. The results in FIG. 3(A) show that 3 anthrone-positive peaks eluted, but only peaks I (PS-I) and II (PS-II) were analyzed further because peak III did not cause C4 consumption.

Figure 3B:
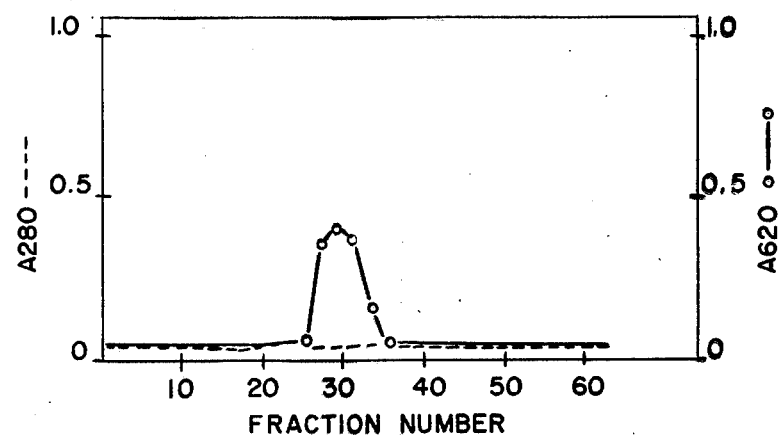
FIG. 3(B) shows that peak II eluted at the same position after rechromatography on the same column. Column, 1.1×70 cm; buffer, 5 mM sodium phosphate, 150 mM NaCl, pH 7.5; flow rate, 6 ml/hr.
Figure 4:
FIG. 4. Disc electrophoresis of pooled and concentrated fractions within peaks I and II from FIG. 3(A). All gels were stained with periodic acid Schiff (PAS) reagent. Gel no. 1, concentrated peak I; gel no. 2, peak I diluted 1:10, gel no. 3, peak I diluted 1:20; gel no. 4, peak I diluted 1:40; gel no. 5, peak II. The arrows point to PAS-positive bands, and demonstrate the heterogeneity of the polysaccharide.

The anthrone-positive peaks PS-I and PS-II were pooled separately, concentrated by ultrafiltration (Amicon UM-2 membrane) at 4° C., and reapplied to the same column. Both peaks eluted in the same position as before. Thus, peak PS-II was significantly lighter than PS-I (FIG. 3B). The molecular weight was estimated to be 3000 daltons by the method of Andrews (1964). The individual fractions within the peaks were pooled, concentrated, and applied to polyacrylamide gels. FIG. 4 (gel no. 1) shows that concentrated PS-I was heterogeneous, and individual bands were not distinguishable after staining the gel with PAS. Gels no. 2, 3, and 4 are concentrated PS-I diluted in saline 1:10, 1:20, and 1:40, respectively. Much of PS-I did not enter the gel or remained in the top portions, and in addition, a diffuse more anodal band is shown in gels no. 1, 2, and 3 (arrows). PS-II (gel no. 5) also was heterogeneous in the gel. A portion of the PS remained on the top of the gel, and 2 bands (arrows) were distinguishable within the gel.

SUGAR COMPOSITION OF THE VENOM PS

The concentrated fractions within peak PS-I (FIG. 3A) were analyzed for individual sugars by gas chromatography, and compared with the ethanol precipitate of the venom. Table 2 shows that 6 sugars were identified: mannose, N-acetylglucosamine, galactose, fucose, N-acetylgalactosamine, and glucose. Mannose was present in the highest concentration, and glucose the least in concentration.

The alcohol precipitate of the venom, which had all of the polysaccharide and only a small portion of the total protein, also contained the same sugars by gas chromatographic analysis, and approximately the same molar ratio as PS-I. Since the protein(s) that remained after alcohol precipitation of the venom was anodalmigrating in polyacrylamide and did not stain with PAS (FIG. 2, gels no. 2 and no. 5), it is probable that the sugars that were measured by gas chromatography were from the PS and not from a glycoprotein(s).

In addition to the neutral sugars, a high content of hexuronic acid also was present in both PS-I and the alcohol precipitate, which explains the source of the net negative charge of the polysaccharide.

In other preliminary chemical assays with PS-I and the alcohol precipitate, they were not precipitated by barium salts, showing no apparent sulfate groups, and they were negative for phosphate content (Ames & Dubin, 1960).

IR SPECTRA

An IR spectrograph was run on neat purified material. As would be expected, only three major peak were obtained. These are tabulated in Table 3.

ELEMENTAL ANALYSIS (CHO)

The purified material eluted from the Sepharose—Con A column and the alcohol precipitate (before purification in the Sepharose—Con A column) from three separate lots of venom extract were sent to Galbraith Laboratories, Inc., Knoxville, Tenn., for elemental analysis. The results are tabulated in Table 4.

SOLUBILITY

To 3 ml of native ant venom (Lot 080678-WA) was added 27 ml of ice-cold absolute ethyl alcohol with stirring at 0° C. to precipitate the active polysaccharide. A light precipitate formed, and the material was centrifuged in 6 tubes containing 5 ml each (International PR-2, 2000 RPM, 10 min., 0° C.). The ehtanol was decanted, the six precipitates were dispersed at the bottom of each tube, and 5 ml of the following solvents were added: acetone, benzene, chloroform, anhydrous ethyl ether, propylene glycol, or glycerol. After mixing, the solubility of the precipitates was determined by visual inspection, at 25° C.

The results tabulated in Table 5 wherein insoluble means at least substantially insoluble; most of the material was apparently not dissolved. Soluble means most of the material appeared to be in solution.

REFERENCES

Ames, B. N. & Dubin, D. T. (1960). The role of polyamines in the neutralization of bacteriophage deoxyribonucleic acid. J. Biol. Chem 235:769–775.

Andrews, P. (1964). Estimation of the molecular weights of proteins by Sephadex gel filtration. Biochem. J. 91:222–233.

Bitter, T. & Muir, H. M. (1962). A modified uronic acid carbazole reaction. Anal. Biochem. 4:330–334.

Davis, B. J. (1964). Disc electrophoresis. Ann. N.Y. Acad. Sci. 121:305–342.

Greenfield, S., Norton, W. T. & Morell, P. (1971). Quaking mouse: isolation and characterization of myelin protein. J. Neurochem. 18:2119–2128.

Griggs, L. J., Post, A., White, E. R., Finkelstein, J. A., Moeckel, K. G., Holder, K. G., Zarembo, J. E., and Weiback, J. A. (1971). Identification and quantitation of alditol acetate of neutral and amino sugar from mucins by automated gas-liquid chromatography. Anal. Biochem. 43:369–381.

Ornstein, L. (1964). Disc electrophoresis. Ann. N.Y. Acad. Sci. 121:305–342.

Segrest, J. P. & Jackson, R. L. (1972). Molecular weight determinations of glycoproteins by polyacrylamide gel electrophoresis in sodium dodecyl sulfate. Methods in Enzymol. 28:54–63.

Seifter, S., Dayton, S., Novic, B. & Muntwyler, E. (1950). The estimation of glycogen with the anthrone reagent. Arch. Biochem. Biophy. 25:191–200.

TABLE 1

Consumption of C4 in normal human serum by eluates of polyacrylamide gel slices containing the isolated polysaccharide from ant venom (see FIG. 2). Equal volumes of each eluate and the serum were incubated at 37° C. for 4 hr, and the C4 titer was determined by functional hemolytic assays.

| Migration Distance (mm) | $CH_{50}$ Units/ml of C4 in Serum |
|---|---|
| 1–3[a] (Top) | 200 |
| 4–5 | 25,000 |
| 7–10 | 50,000 |
| 11–18 | 6,500 |
| 30–35 | 500,000 |
| 45–50 | 500,000 |
| 72–75 (Bottom) | 500,000 |
| Buffer | 500,000 |

TABLE 1-continued

Consumption of C4 in normal human serum by eluates of polyacrylamide gel slices containing the isolated polysaccharide from ant venom (see FIG. 2). Equal volumes of each eluate and the serum were incubated at 37° C. for 4 hr, and the C4 titer was determined by functional hemolytic assays.

| Migration Distance (mm) | $CH_{50}$ Units/ml of C4 in Serum |
|---|---|
| Control | |

[a] Contains both the PAS-staining material that did not enter the gels, and the first band within the gels.

TABLE 2

Sugar composition and the molar ratios of the native ant venom in Peak I (FIG. 3A) and the alcohol precipitate of the venom as determined by gas chromatography.

| | MOLAR RATIOS | |
|---|---|---|
| Sugar | PI of G-25[a] (EtOH ppt.) | PI of G-25[a] (Native) |
| Fucose | 1.5 | 1.8 |
| Mannose | 9.0 | 7.7 |
| Galactose | 1.1 | 1.4 |
| Glucose | 1.2 | 1.0 |
| N-acetyl glucosamine | 1.0 | 1.0 |
| N-acetyl galactosamine | 1.2 | 1.6 |

[a] Peak I from elution of Sephadex G-25 column (see text for details).

TABLE 3

INFRARED

| Description of Peak | Relative Height (Approx) | |
|---|---|---|
| | [1]Alcohol ppt | [2]man. eluate |
| Broad peak centered about 3460 cm - 1 | 8 | 5 |
| Broad peak centered about 2100 cm - 1 | 1 | 3 |
| Medium peak centered about 1640 cm - 1 | 5 | 2 |

Figure 5:
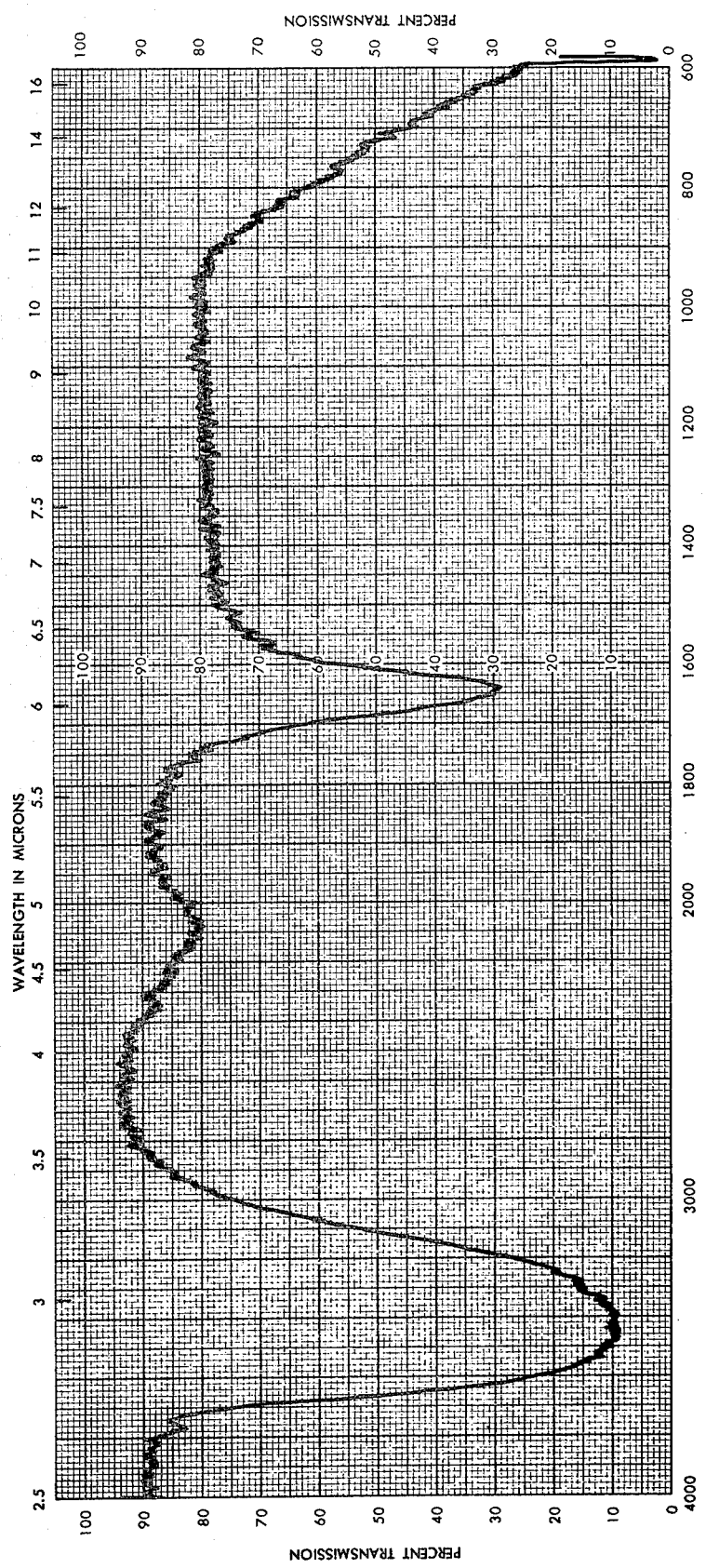
FIG. 5 is a typical IR Spectra run neat on an alcohol precipate of ant venom extract.
Figure 6:
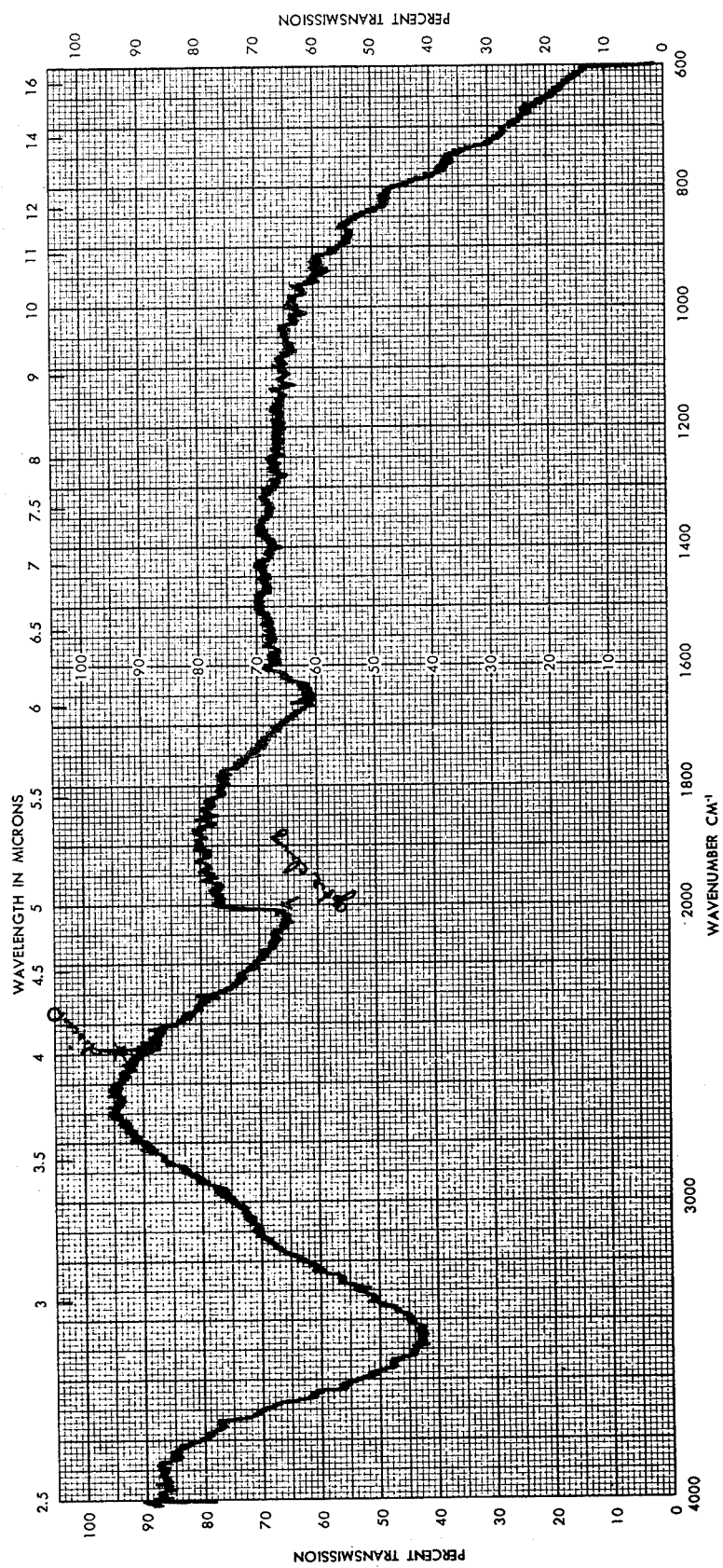
FIG. 6 is a typical IR Spectra run neat on an α D-mannoside eluate of Con A column of the alcohol precipitate.

[1]Alcohol precipitate of ant venom from 500 ants (see FIG. 5)
[2]α D-Mannoside eluate of Con A column of alcohol precipitate (see FIG. 6)

TABLE 4

ELEMENTAL ANALYSIS

| Composition of Sample | % C | % H | % O |
|---|---|---|---|
| EtOH ppt. of venom lot 052778 | 41.19 | 6.08 | 37.62 |
| Same as 1, but Con A-Seph. eluate | 43.15 | 7.04 | 42.66 |
| EtOH ppt. of venom lot 080678 | 37.15 | 5.81 | 35.75 |
| Same as 3, but Con A-Seph. eluate | 43.53 | 7.30 | 36.19 |
| EtOH ppt. of venom lot 082678 | 37.70 | 6.50 | 35.60 |
| Same as 5, but Con A-Seph. eluate | 37.29 | 6.35 | 37.80 |

TABLE 5

SOLUBILITY

| Solvent | Effect |
|---|---|
| Ethyl alcohol | Insoluble |
| Acetone | Insoluble |
| Benzene | Insoluble |
| Chloroform | Insoluble |
| Ethyl ether | Insoluble |
| Propylene glycol | Soluble |
| Glycerol | Soluble |
| Water | Soluble |
| Phosphate or acetate buffers in water, pH range 3 to 11 | Soluble |

What is claimed is:

1. A product for the treatment of rheumatoid arthritis, characterized by:
   (a) a negative stain test for proteins with Amido Black 10B;
   (b) a positive stain test for glycoprotein and polysaccharide with periodic acid Schiff reagent (PAS), the combination of tests (a) and (b) leading to the conclusion that the composition is of a polysaccharide nature;
   (c) the consumption of $C_4$ (human blood complement system) upon incubation with human blood serum at 375° C. for 4 hours;
   (d) a positive test for neutral sugars with anthrone reagent;
   (e) a positive test for hexuronic acids by carbazole method of Bitter and Muir;
   (f) not being precipitated from aqueous solution by barium salts, indicating the apparent absence of sulfate groups;
   (g) a negative phosphate test by the method of Ames and Dubin;
   (h) substantial solubility in propylene glycol, glycerol, water, phosphate buffers (aqueous) pH 3 to 11, and acetate buffers (aqueous) pH 3 to 11;
   (i) substantial insolubility in ethyl alcohol, acetone, benzene, chloroform and ethyl ether;
   (j) approximate sugar molar ratios:

| Sugar | Molar Ratio Range |
   |---|---|
   | Fucose | approximately 1-2 |
   | Mannose | approximately 8-9 |
   | Galactose | approximately 1-15 |
   | Glucose | approximately 1 |
   | N-acetyl glucosamine | approximately 1 |
   | N-acetyl galactosamine | approximately 1-2 |

(k) an approximate elemental analysis (CHO) of 35-45% carbon, 6-7% hydrogen and 35-43% oxygen; and
   (l) an infrared spectrograph showing three major peaks approximately centered about 3460 $cm^{-1}$, 2100 $cm^{-1}$ and 1640 $cm^{-1}$ as defined in FIG. 5.

2. The product of claim 1 further characterized by having been extracted from the venom of ants of the species triplarinus, genus Pseudomyrmex.

3. An injectible composition for the treatment of rheumatoid arthritis comprising an effective amount for the treatment of rheumatoid arthritis of the product of claim 1 in a pharmaceutically acceptable carrier.

4. A method for treatment of rheumatoid arthritis in a patient comprising administering by injection to said patient, an effective amount for the treatment of rheumatoid arthritis of the product of claim 1.

* * * * *

UNITED STATES PATENT AND TRADEMARK OFFICE
CERTIFICATE OF CORRECTION

PATENT NO. : 4,247,540
DATED : January 27, 1981
INVENTOR(S) : Gunter Holzmann

It is certified that error appears in the above—identified patent and that said Letters Patent is hereby corrected as shown below:

Claim 1, Col. 22, Line 22, change "375°C." to --37°C.--

Signed and Sealed this

Fifth Day of May 1981

[SEAL]

Attest:

RENE D. TEGTMEYER

Attesting Officer     Acting Commissioner of Patents and Trademarks